US012005385B2

(12) United States Patent
Ko et al.

(10) Patent No.: US 12,005,385 B2
(45) Date of Patent: Jun. 11, 2024

(54) STRETCHER OF ELASTIC MATERIAL, AIR FILTER UNIT CAPABLE OF CONTROLLING AIR PERMEABILITY INCLUDING SAME, AND MASK INCLUDING THE AIR FILTER UNIT

(71) Applicant: SEOUL NATIONAL UNIVERSITY R&DB FOUNDATION, Seoul (KR)

(72) Inventors: Seung Hwan Ko, Seoul (KR); Jaeho Shin, Incheon (KR); Seong Min Jeong, Seoul (KR); Jinmo Kim, Seoul (KR); Joonwha Choi, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 748 days.

(21) Appl. No.: 17/267,871

(22) PCT Filed: Nov. 17, 2020

(86) PCT No.: PCT/KR2020/016150
§ 371 (c)(1),
(2) Date: Feb. 11, 2021

(87) PCT Pub. No.: WO2021/206256
PCT Pub. Date: Oct. 14, 2021

(65) Prior Publication Data
US 2022/0111325 A1    Apr. 14, 2022

(30) Foreign Application Priority Data

Apr. 6, 2020 (KR) .................. 10-2020-0041700
May 29, 2020 (KR) .................. 10-2020-0064678
Jul. 27, 2020 (KR) .................. 10-2020-0092867

(51) Int. Cl.
*B01D 46/42*   (2006.01)
*A41D 13/11*   (2006.01)
(Continued)

(52) U.S. Cl.
CPC .......... *B01D 46/4227* (2013.01); *A41D 13/11* (2013.01); *A61L 2/10* (2013.01);
(Continued)

(58) Field of Classification Search
CPC .............. B01D 46/4227; B01D 46/543; B01D 24/00–4892; B01D 25/00–386;
(Continued)

(56) References Cited

U.S. PATENT DOCUMENTS

2017/0050056 A1*   2/2017   Xu ........................... A62B 7/10

FOREIGN PATENT DOCUMENTS

JP    2012-130827 A       7/2012
JP    2012130827 A    *   7/2012
(Continued)

OTHER PUBLICATIONS

Translation of JP-2012130827-A. Accessed from Espacenet on Jan. 18, 2024. (Year: 2012).*

*Primary Examiner* — Valerie L Woodward
*Assistant Examiner* — Paige Kathleen Bugg
(74) *Attorney, Agent, or Firm* — Hauptman Ham, LLP

(57) ABSTRACT

A mask according to an embodiment of the present disclosure may adjust permeability thereof by including and using an air filter unit which is capable of expanding or contracting, in at least one direction, a filter for filtering particles contained in air passing through the mask by pores.

18 Claims, 22 Drawing Sheets

(51) Int. Cl.
  *A61L 2/10* (2006.01)
  *A62B 23/02* (2006.01)
  *B01D 46/00* (2022.01)
  *B01D 46/54* (2006.01)

(52) U.S. Cl.
  CPC ........ *A62B 23/025* (2013.01); *B01D 46/0028* (2013.01); *B01D 46/543* (2013.01); *A61L 2202/11* (2013.01); *B01D 2279/40* (2013.01)

(58) Field of Classification Search
  CPC ...... B01D 27/00–148; B01D 33/00–82; B01D 35/00–34; B01D 2275/302; A62B 23/00–06; A62B 7/10; A62B 18/02–10; A41D 13/11–1192
  USPC .................................................... 128/206.19
  See application file for complete search history.

(56) References Cited

FOREIGN PATENT DOCUMENTS

| | | |
|---|---|---|
| KR | 10-0813114 B1 | 3/2008 |
| KR | 10-2014731 B1 | 8/2019 |
| KR | 10-2020-0020747 A | 2/2020 |

\* cited by examiner (a)

(b)

(c)

(a)

(b)

(a)

(b)

STRETCHER OF ELASTIC MATERIAL, AIR FILTER UNIT CAPABLE OF CONTROLLING AIR PERMEABILITY INCLUDING SAME, AND MASK INCLUDING THE AIR FILTER UNIT

CROSS-REFERENCE TO RELATED APPLICATION

The present application is a national stage filing under 35 U.S.C. § 371 of PCT application number PCT/KR2020/016150 filed on Nov. 17, 2020, which is based upon and claims the benefit of priorities to Korean Patent Application No. 10-2020-0041700, filed on Apr. 6, 2020, Korean Patent Application No. 10-2020-0064678, filed on May 29, 2020, and Korean Patent Application No. 10-2020-0092867, filed on Jul. 27, 2020, in the Korean Intellectual Property Office, which are incorporated herein in their entireties by reference.

TECHNICAL FIELD

The present invention relates to a stretcher made of an elastic material, an air filter unit capable of controlling air permeability including the same, and a mask and including the air filter unit.

BACKGROUND ART

Interest is growing in personal protective equipment (PPE) including masks and the like due to the problem of worsening of air quality caused by yellow dusts (PM 10) and fine dusts (PM 2.5) and the problem of COVID-19 attacking the whole world in 2020.

Accordingly, many technologies regarding PPE are being developed or have already been developed and sold in market. Most PPE is concentrated on protection of a user and has the problem in that the problem of user convenience or the problem of adaptability for adaptation to a change in surrounding environments cannot almost be considered. The same problems apply masks. However, masks are distinguished from PPEs of other types by being used even by various age groups and basal patients. In case of the elderly and infirm or respiratory basal patients, it has been reported that mask wearing may rather cause a problem in health, such as a cardiopulmonary dysfunction, and even in case of a healthy adult, physical activity is restricted due to limited oxygen supply caused by mask wearing.

Furthermore, the higher the filtering performance of masks, the more the exhalation is trapped in a space between masks and face. The trapped exhalation causes unpleasant feeling such as smell, humidity, or temperature. Such unpleasant feeling causes resistance to mask wearing and acts as a limitation from a public health standpoint.

In particular, masks are important not only for ordinary persons but also for healthcare providers, and medical masks are bound to be more firmly brought into contact with faces and have low permeability. That is, since healthcare providers should always wear masks having the highest level filtering performance even in low-risk places, tiredness due to mask wearing is bound to be high for healthcare providers. Recently, there are attempts to assist permeability by providing a fan to a medical mask, but there are limitation in that The self weight of the mask increases due to the weight of components for driving the fan, the operation time is short, and smooth communication between healthcare provides is not easy due to noises occurring when driving the fan.

Consequently, since masks have no adaptability to a change in environment surrounding users, users have problems in that it is difficult to always wear masks.

DISCLOSURE OF THE INVENTION

Technical Problem

One objective of the present invention is to provide a stretcher capable of expanding an elastic material present at the center. In particular, the present invention provides a stretcher capable of stretching the elastic material present at the center in an isotropic mariner.

In addition, another objective of the present invention is to provide an air filter unit capable of adjusting permeability according to a change in peripheral environment using the stretcher. In particular, the objective of the stretcher used for the air filter according to the present invention is not to interfere with movements of a wearer by a simple structure of the stretcher when the stretcher is installed on a mask.

Eventually, the objective of the present invention is to provide a mask that has the air filter unit and that can be comfortably worn by a wearer for a long time during various activities due to permeability adjustment.

Meanwhile, other unspecified objectives of the present invention will be further considered within a scope which can be easily inferred from the detailed descriptions below and the effects thereof.

Technical Solution

In order to achieve the above objectives, there is proposed a stretcher capable of expanding an elastic material. According to an embodiment of the present invention, a stretcher capable of expanding an elastic material located at a center thereof, the stretcher includes a variable part installed around the elastic material and configured to pull at least one side of the elastic material and expand the elastic material, wherein the variable part includes a first wall connected to the elastic material and having elasticity, and a second wall constituting a hollow hole together with the first wall, the first wall is extended toward the hollow hole as air escapes from the hollow hole, and the first wall expands the elastic material as the first wall is extended toward the hollow hole.

An air filter unit according to another embodiment of the present invention uses the stretcher according to the above described embodiment. According to another embodiment of the present invention, an air filter unit capable of adjusting permeability by including a filter configured to filter particles contained in passing air by pores and a stretcher capable of expanding or contracting the filter in at least one direction, wherein: the filter is formed of an elastic material and has pores the sizes of which vary according to an operation of the stretcher; the stretcher includes a membrane in which the filter is installed and a variable part installed around the membrane and configured to pull at least one side of the membrane and expand the elastic material; the variable part includes a first wall connected to the membrane and having elasticity and a second wall constituting a hollow hole together with the first wall; the first wall is extended toward the hollow hole as air escapes from the hollow hole; the first wall expands the membrane as the first wall is extended toward the hollow hole; and the pores of the filter are expanded depending on the expansion of the membrane.

A mask according to still another embodiment of the present invention uses the air filter unit according to the another embodiment. According to still another embodiment of the present invention, a mask includes: a mask body configured to cover the nose and mouth of a wearer; an air filter unit installed to the mask body; and a fixing member formed on both sides of the body and configured to fix the body to the face of the wearer, wherein: the air filter unit includes a filter configured to filter particles contained in passing air by pores and a stretcher capable of expanding or contracting the filter in at least one direction; the filter is formed of an elastic material and has pores the sizes of which vary according to an operation of the stretcher; the stretcher includes a membrane in which the filter is installed and a variable part installed around the membrane and configured to pull at least one side of the membrane and expand the elastic material; the variable part includes a first wall connected to the membrane and having elasticity and a second wall constituting a hollow hole together with the first wall; the first wall is extended toward the hollow hole as air escapes from the hollow hole; the first wall expands the membrane as the first wall is extended toward the hollow hole; and the pores of the filter are expanded depending on the expansion of the membrane.

Advantageous Effects

A stretcher according to an embodiment of the present invention is formed by a first wall that has ring-shaped variable part having elasticity and connected to an inside elastic material and a second wall that constitutes a hollow hole together with the first wall, and is configured so as to partition the hollow hole into a first space and a second space by a partition wall having a connection hole formed therein. At least a portion of the second space is formed by the first wall, the first wall is extended toward the second space by escapement of air from the second space to the first space according to a movement of a sealing member formed in the first space, and the first wall extends an elastic material while the first wall is extended toward the first space side. In particular, the stretcher according to the embodiment of the present invention has advantage of being lightweight, having a simple structure, being capable of simply adjusting a movement of a sealing member using a lever or the like.

An air filter unit according to another embodiment of the present invention may adjust permeability by changing the sizes of pores formed in a filter made of elastic material according to an operation of a stretcher using the stretcher of the one embodiment and a filter made of an elastic material. That is, in the air filter unit according to another embodiment of the present invention, when the state of peripheral air is bad, the capability of filtering particles is enhanced by reducing the sizes of pores, and when the state of peripheral air is good, the amount of air introduced or discharged air by increasing the sizes of pores.

A mask according to another embodiment of the present invention is provided with the above-described air filter unit, and provides variability according to the state of peripheral air, and thus, a wearer may guide a wearer to always wear the mask. That is, when an increase in breathing quantity is allowed in case in which a user takes exercise or the state of peripheral air is good, permeability is enhanced by increasing the sizes of pores, and when there is risk of strong fine dust, virus, or the like, capability of filtering particles may be improved by reducing the sizes of pores, and thus, stability may be enhanced. Furthermore, the mask according to another embodiment of the present invention has advantage in that the sizes of pores may actively be adjusted together with a sensor for sensing the state of peripheral air.

Meanwhile, even though an effect is not specifically described herein, the effect described in the description below and expected by the technical feature of the present invention and a temporary effect thereof will be considered as being described in the specification of the present invention.

BRIEF DESCRIPTION OF THE DRAWINGS

FIG. 1(a) shows a 3D image illustrating air flow near the pores of the filter, FIG. 1(b) shows a schematic cross-sectional view of streamlines in the pores of the filter, and FIG. 1(c) schematically illustrating, together with streamlines, the behavior of floating particles contained in air at a position near the pores.

It is clarified that the attached drawings are illustrated as a reference for understanding the technical concept of the present invention, and the scope of the present invention is not limited by the drawings.

MODE FOR CARRYING OUT THE INVENTION

Hereinafter with reference to drawings, the configuration of the present invention introduced by various embodiments of the present invention, and the effect due to the configuration will be described. In describing the present invention, detailed descriptions related to well-known functions and matters obvious to a person skilled in the art will be ruled out when the functions and matters unnecessarily obscures the subject matters of the present invention.

The "pores" of a filter means holes to voids through which air passes, and includes, for example, holes formed by various fibers or holes formed in a flat plate.

Figure 1:
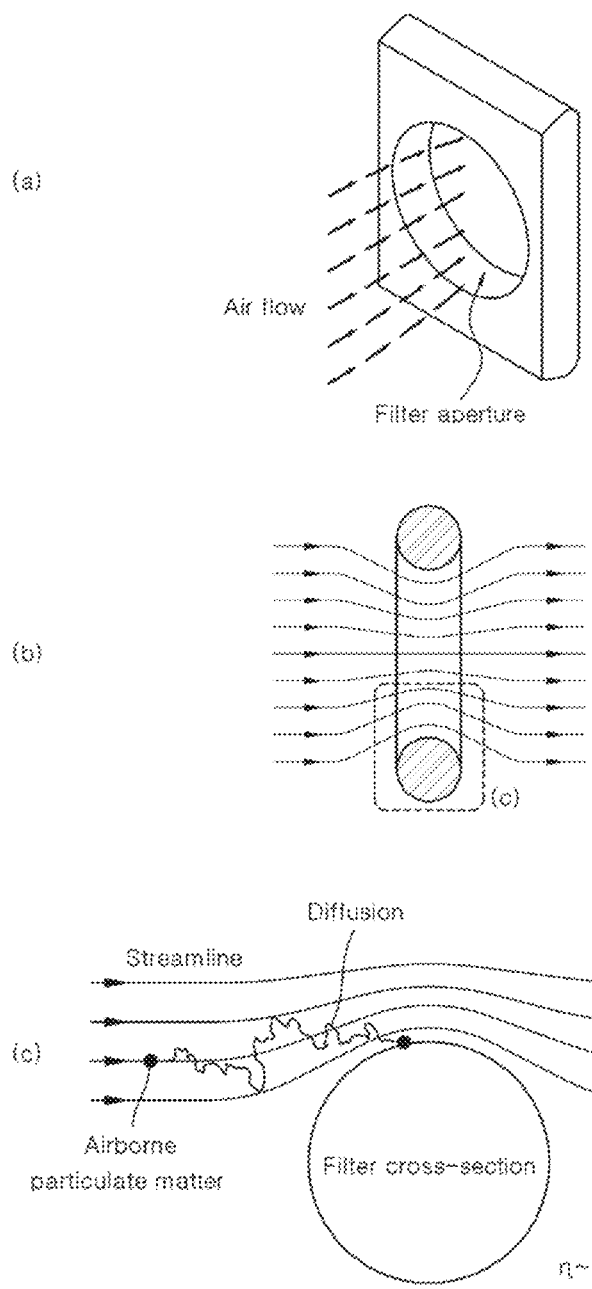
FIG. 1 is a referential view for explaining a principle of filtering particles passing through pores in a filter.

In order to more clearly explain the present invention, a principle of an air filter unit will first be described with reference to FIG. 1, in which air introduced through pores (2) formed in a filter (1) flows along streamlines. Floating particles (for example, fine dusts, ultrafine dusts or droplets) also pass through the pores along the streamlines. Floating particles deviates from the streamlines due to diffusion and an effect of electrostatic attraction force and are filtered by making contact with and mounted onto the inner walls of pores due to such deviation. The smaller the sizes of the pores, the greater the floating particles have probability of being filtered, and conversely, the lower the permeability. As explained in the background art, the deterioration in permeability is likely to cause various problems to a wearer. Air filter units and masks according to the present invention to be described below are configured such that filtering capability and permeability can be adjusted according to peripheral states, and thus, the problems of conventional air filters and masks are to be solved.

Hereinafter, air filter units and masks according to the present invention will be described with reference to accompanying drawings.

Figure 2:
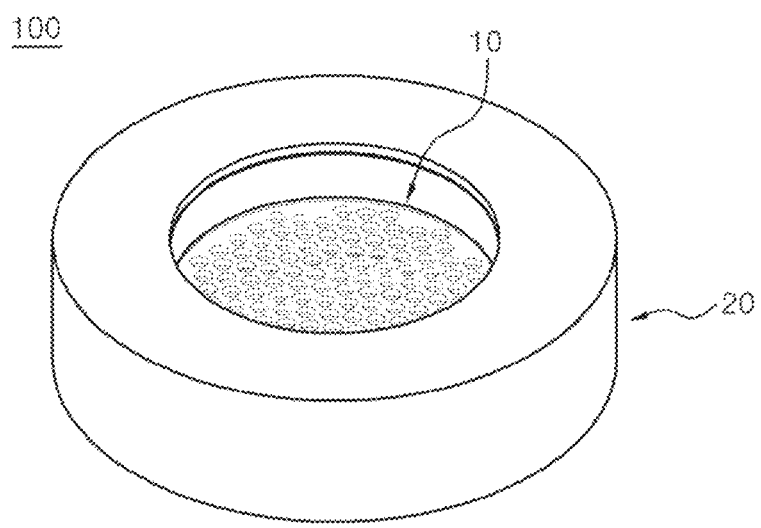
FIG. 2 is a schematic perspective view of an air filter unit according to an embodiment of the present invention.
Figure 3:
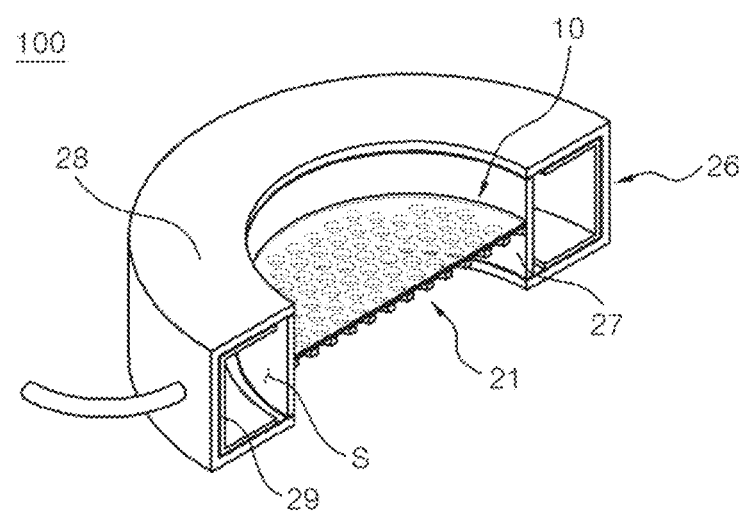
FIG. 3 is a schematic cross-sectional perspective view of an air filter unit according to an embodiment of the present invention.
Figure 4:
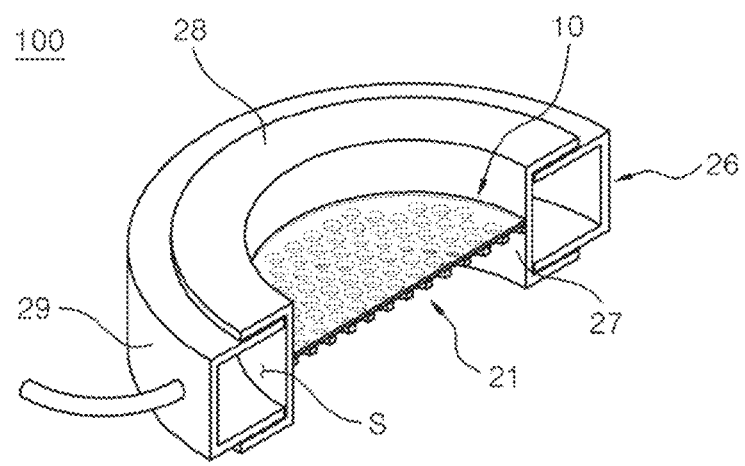
FIG. 4 is a schematic cross-sectional perspective view of an air filter unit according to another embodiment of the present invention.

FIG. 2 is a schematic perspective view of an air filter unit according to an embodiment of the present invention, FIG. 3 is a schematic cross-sectional perspective view of an air filter unit according to an embodiment of the present invention, and FIG. 4 is a referential view for explaining installation of a filter to a membrane of an air filter.

An air filter unit 100 according to an embodiment of the present invention is composed of a filter 10 and a stretcher 20.

Pores are formed in the filter 10, and the filter is expanded or contracted by the stretcher 20 in at least one direction, thereby adjusting permeability of the filter. The filter 10 is also important to achieve an effect to be provided by an air filter unit 100 in which filtering capability and permeability can be adjusted according to peripheral states, and thus, the manufacturing method and materials for the filter 10 will be described later in detail. Meanwhile, expansion or contraction means that the filter 10 is expanded or contracted relatively with respect to one state. That is, when the most contracted state serves as a reference, only expansion will be possible, and when the most expanded state serves as a reference, only contraction will be possible.

The stretcher 20 is composed of a membrane 21 and a variable part 26.

The filter 10 is installed to the membrane as shown in FIG. 4. Installation of the filter to the membrane 21 means causing the filter 10 to be in close with the membrane 21. At this point, close contact may be achieved by intermolecular force, electrostatic attractive force, or separate adhesives. However, the "close contact" in the present invention is not limited to such examples, and means that the filter 10 is attached by such a degree that the filter 10 follows the movement of the membrane 21.

Figure 5:
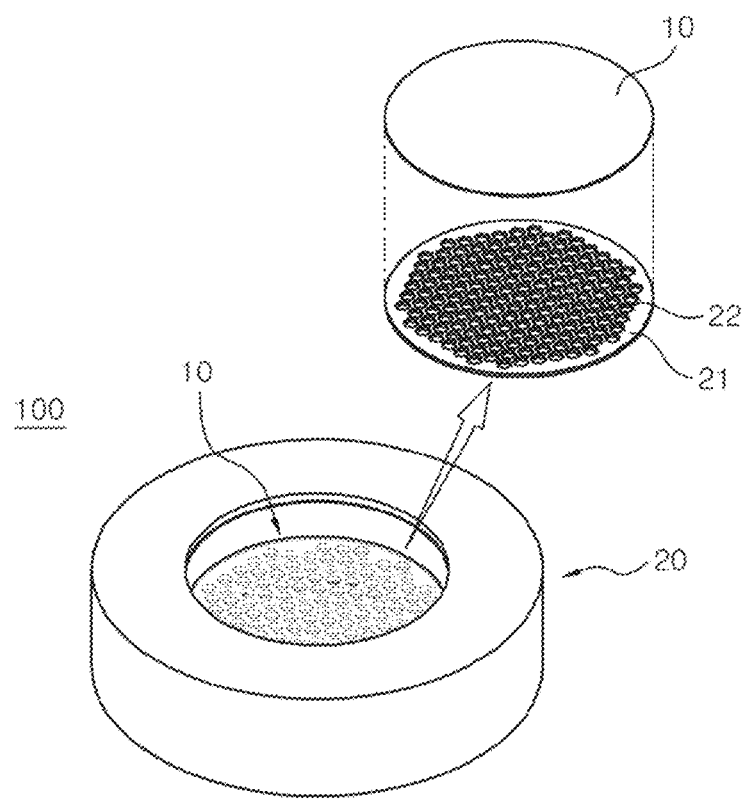
FIG. 5 is a referential view for explaining installation of an air filter to a membrane.

The central section of the membrane 21 may be formed in a mesh shape. That is, as shown in FIG. 4, holes 22 through which air introduced to the filter 10 passes are formed in the membrane 21. Important thing is that a frame constituting the holes 22 of the central section of the membrane 21 makes close contact (see FIG. 5) with the filter 10, and the force transmitted to the membrane 21 is transmitted to the filter 10. Thus, the present invention is not limited by the shapes or sizes of the holes 22. For example, a form may be possible in which the central section of the membrane 21 does not have a mesh shape but has a large hollow hole formed therein, and the filter 10 installed only in an edge portions of the membrane 21.

The variable part 26 is installed around the membrane 21. The variable part 26 isotroptically pulls or pushes at least one side or periphery of the membrane 21 to expand or contract the membrane 21. Expanding or contracting the membrane 21 means that the filtering efficiency or permeability of the filter 10 is eventually changed.

As described above, the variable part 26 may be configured to pull at least one side of the membrane 21. When the variable part 26 is configured to pull at least one side of the membrane 21, it is desirable to fix the other side of the membrane 21. If the other side of the membrane 21 is not fixed, even when the one side of the membrane 21 is pulled, the sizes of the pores of the filter 10 are not changed because there is a change in the shape of the membrane, but no change in the area of the membrane 21. Consequently, the variable part 26 pulls or pushes one side of he membrane 21, so that the area of the membrane 21 is changed by the variable part 26 because the other side of the membrane is configured to be in a fixed state.

It is more desirable to isotropically pull or push the membrane 21 by the variable part 26 than to pull or push only one side of the membrane 21 by the variable part 26. This is because a change in the membrane 21 may be maximized. For example, when the membrane 21 is a circular plate having holes formed therein, the entire outer circumference of the membrane 21 may be configured so as to be connected to the variable part 26 or to be connected to the variable part 26 at equal intervals.

The configuration of the variable part 26 will be described with reference to FIG. 3.

The variable part 26 is configured to include a first wall 27 and a second wall 28. The first wall 27 and the second wall 26 constitute a hollow hole S. The first wall 27 is directly connected to the membrane 21 and has elasticity. By comparison, the second wall 28 only constitutes the hollow hole with the first wall 27, but does not have elasticity or the elasticity of the second wall is limited by the fixed wall or a fixed frame 29. That is, the first wall 27 is extended or expanded in one direction or the reverse direction thereof as air escapes from or is injected into the hollow hole S, so that a movement of pulling or pushing the membrane 21 is performed and the area of the membrane 21 is changed. However, the second wall 28 has no change or a very small change by the escapement or injection of air from/to the hollow hole S. It is natural for operation of the variable part 26 that in the hollow hole S, places other than places where air is injected or escapes be sealed. Meanwhile, the positions where the fixed wall or the fixed frame is formed are not important. For example, the fixed wall or the fixed frame 29 may be formed in the inner surface of the second wall 28 or on an outer surface thereof, and it is rather possible to be integrally formed inside the second wall 28. Meanwhile, instead of using the fixed wall or the fixed frame 29, it is also possible that the second wall 28 itself is formed by a non-elastic material.

Meanwhile, unlike the variable part 26 shown in FIG. 3, it is also possible as shown in FIG. 4 to form the hollow hole S by coupling the variable part 26 via the first wall 27 and the fixed frame 29. In this case, the second wall 28 is absent or the second wall merely performs a function to couple the first wall 27 and the fixed frame 29.

Figure 6:
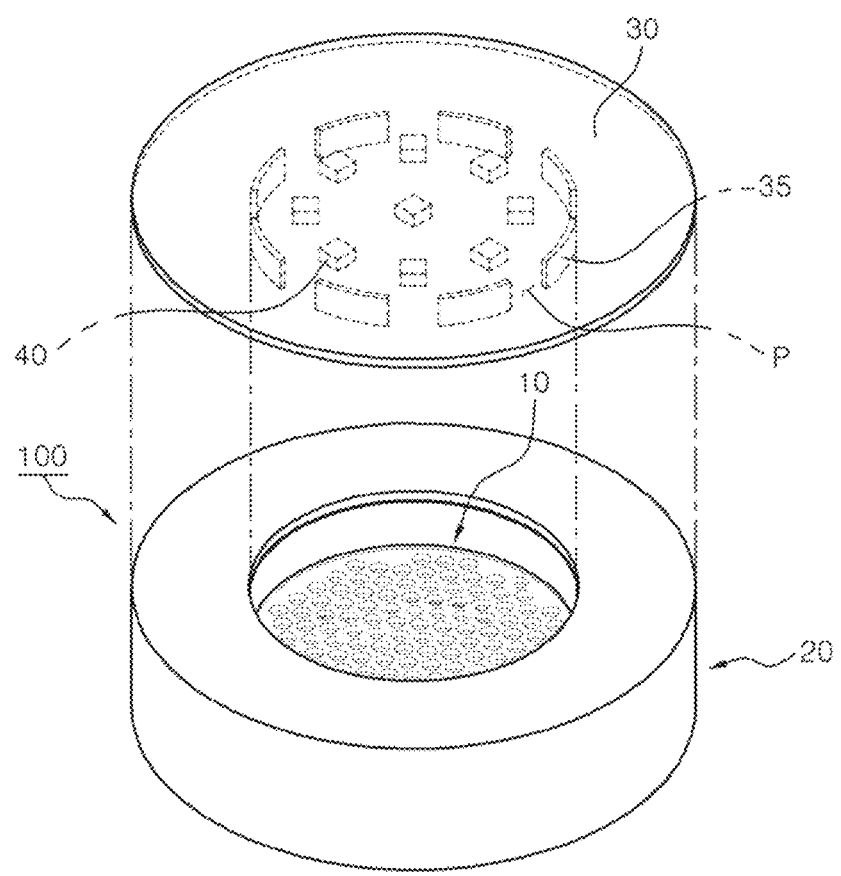
FIG. 6 is a schematic perspective view illustrating an embodiment in which an air filter unit according to the present invention is provided with a lid 30 and a lamp 40 for ultraviolet irradiation.

FIG. 6 is a schematic perspective view illustrating an embodiment in which an air filter unit according to the present invention is provided with a lid 30 and a lamp 40 for ultraviolet irradiation.

Referring to FIG. 6, a lid 30 which is installed at a distance from the filter 10 is formed on the front surface of the filter 10. The lid 30 is spaced apart from the filter by a guide 35 and has an air flow path. P formed between the lid and the guide 35. That is, air flows through the air flow path P through which air is introduced to the filter 10.

A lamp 40 which irradiates the filter 10 with ultraviolet is provided inside the lid 30. When performing the function for purifying air, bacteria or the like are likely to proliferate in the air filter unit 100. The present invention is provided with, in the air filter unit 100, a lamp 40 which irradiates the filter with ultraviolet, and prevents proliferation of bacteria by irradiating the filter 10 with ultraviolet.

FIG. 7(a) illustrates a state of a stretcher when prioritizing the filtering performance of an air filter unit, and FIG. 7(b) illustrates a state of a stretcher when prioritizing permeability of the air filter unit.

Figure 7:
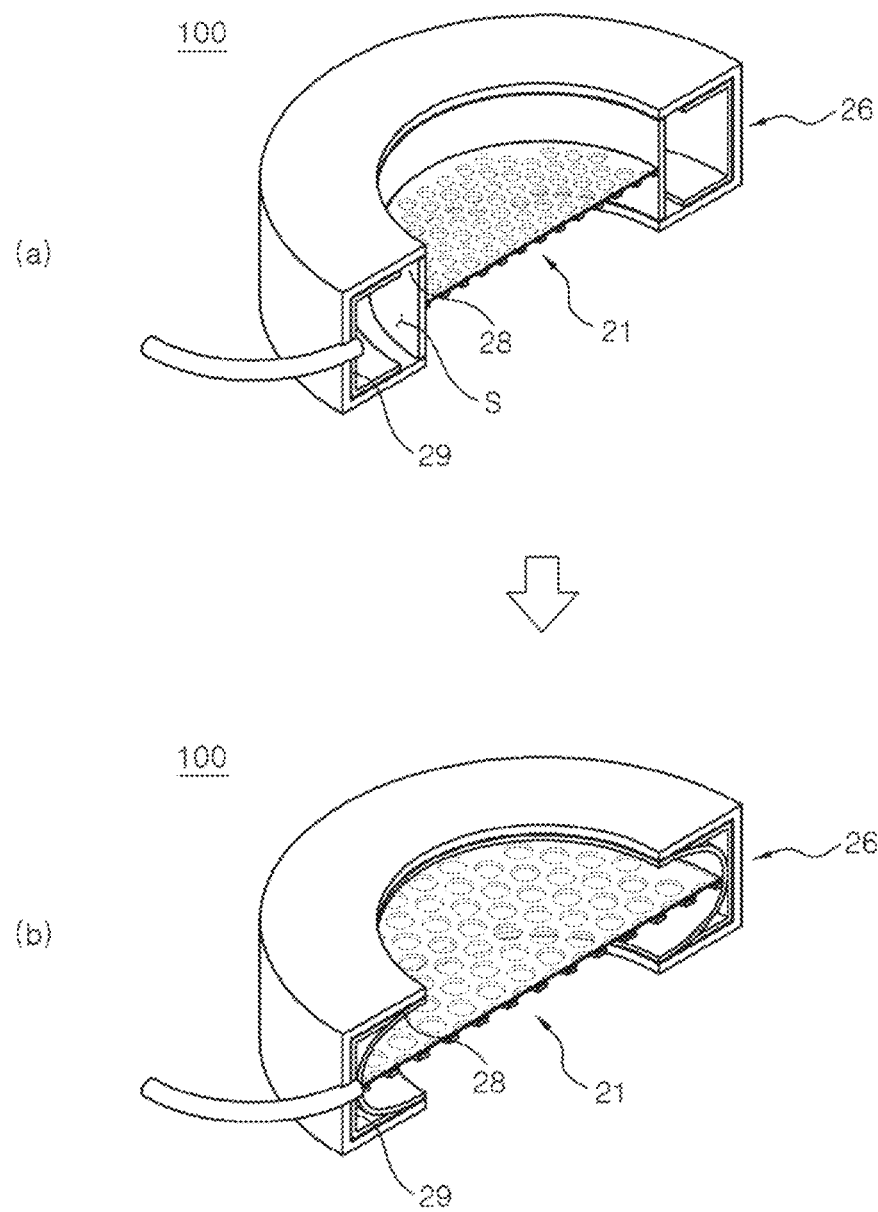
FIG. 7(a) illustrates a state of a stretcher when prioritizing the filtering performance of an air filter.
FIG. 7(b) illustrates a state of a stretcher when prioritizing permeability of the air filter.

In FIG. 7, the stretcher 20 is configured by two states. One state is a first state in a case in which filter performance is prioritized, and means a state in which air in the hollow hole S is neither separately extracted nor injected, and the pores of the filter 10 is minimized, and the other state is a second state and means a state in which the pores of the filter 10 is expanded by the stretcher 20 by extracting the air in the hollow hole S.

Comparing FIGS. 7(a) and 7(b), the hollow hole S is contracted as air escapes from the hollow hole S through a tube. That is, the first wall 27 expands to the inside of the hollow hole S. Since the membrane 21 is connected co the first wall 27, the membrane 21 is expanded as the first wall 27 expands, the filter 10 is expanded as the membrane 21 expands, and thus, pores are expanded.

When air is injected into the hollow hole S through the tube, the first wall returns again to the original state, the membrane 21 is also contracted, the filter 10 is contracted as the membrane 21 is contracted, and thus, the pores are contracted.

Accordingly, since the pores are contracted in the first state, floating particles contained in the air passing through the filter 10 collide with the filter and are more likely to be mounted and collected to the filter, and thus, filtering performance is improved. Conversely, in the second state, since the pores are expanded, the amount of passing air even under the same pressure and permeability is improved. In particular, an air filter unit of the present invention can be used in an intermediate state between the first state and the second state. Thus, the present invention has advantage of having remarkably high adaptability against environments by appropriately operating the air filter unit according to peripheral environments or needs.

That is, filtering capability and permeability of an air filter unit 100 according to an embodiment of the present invention may adjusted according to peripheral environments. In particular, a stretcher 20 used for an air filter unit 100 according to an embodiment of the present invention may isotropically expand or contract a membrane 21 using pneumatic pressure, thereby solving the limitation in which isotropic expansion units used in prior arts depend on complicated machinery. Furthermore, such machinery has the limitation of a heavy, weight and a large volume. Thus, an air filter unit 100 according to an embodiment of the present invention has advantage of being usable for a mask that is lightweight and has small volume and is worn by a person.

Furthermore, when an air filter unit 100 according to another embodiment of the present invention is used as the following, a separate tube, wire or the like is not necessary to control the operation of a stretcher.

Figure 8:
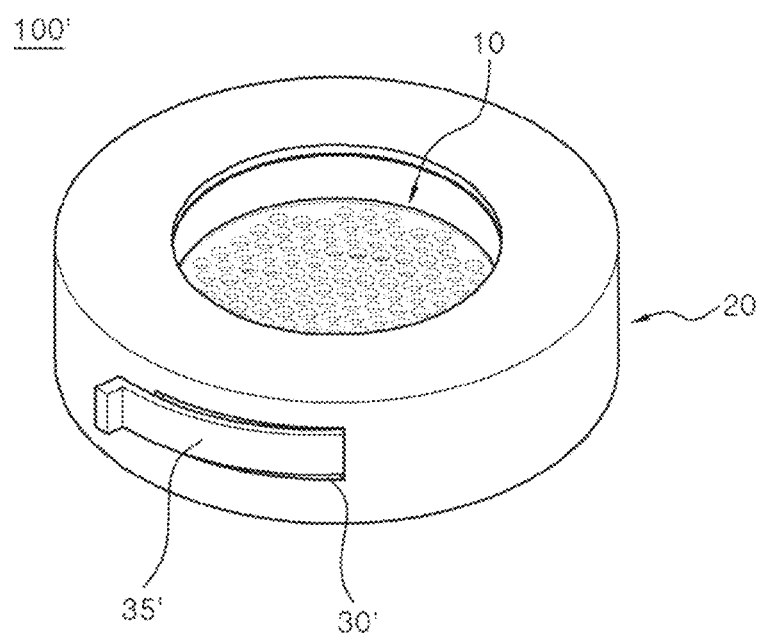
FIG. 8 is a schematic perspective view of an air filter unit according to another embodiment of the present invention.
Figure 9:
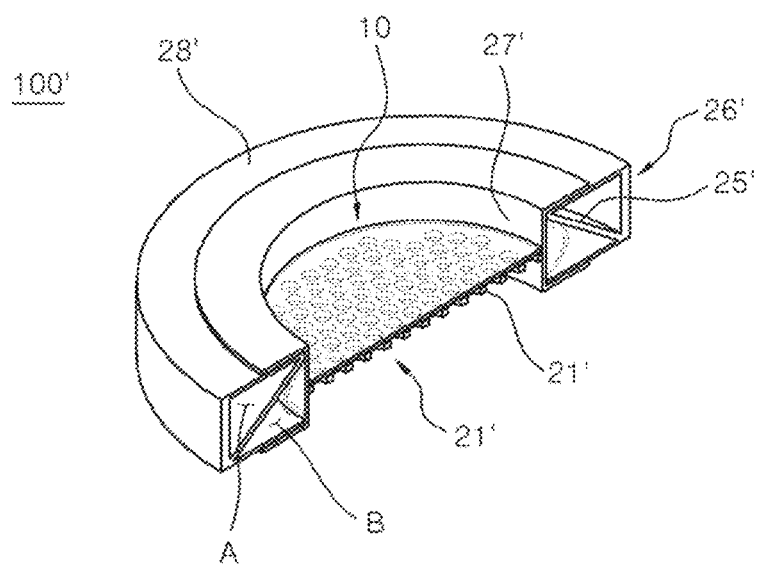
FIG. 9 is a schematic cross-sectional perspective view of an air filter unit according to another embodiment of the present invention.
Figure 10:
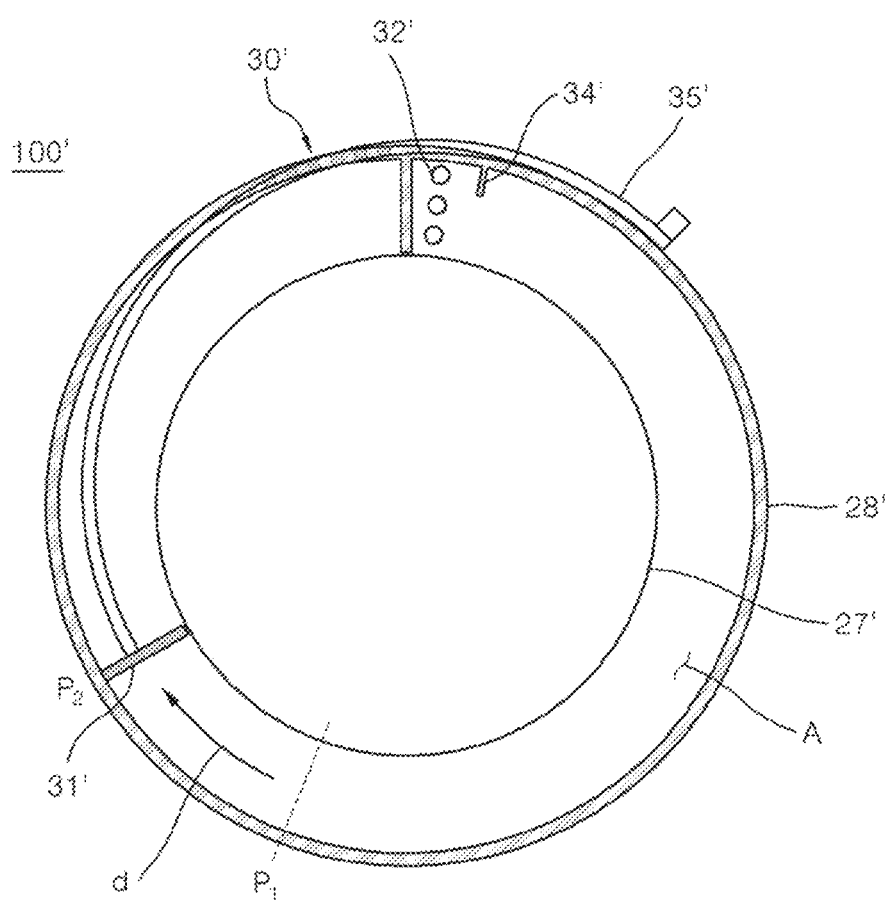
FIG. 10 is a schematic plan view of an air filter unit according to another embodiment of the present invention.

FIG. 8 is a schematic perspective view of an air filter unit 100' according to another embodiment of the present invention, FIG. 9 is a schematic cross-sectional perspective view of an air filter unit 100' according to another embodiment of the present invention, and FIG. 10 is a schematic plan view of an air filter unit 100' according to another embodiment of the present invention.

Referring to FIGS. 8 to 10, in a stretcher 20' of an air filter unit 100' according another embodiment of the present invention, a variable part 26' includes a first wall 27' having elasticity and a second wall 28' constituting a hollow hole together with the first wall 27', wherein unlike the air filter unit 100 described above, a hollow hole is partitioned into a first space A and a second space B by a partition wall 25'.

Meanwhile, the variable part 26' may be formed in a ring shape, and as shown, the cross-section of the ring can have a rectangular or circular shape. However, the embodiment of the present invention is not limited thereto.

An elastic material is located at the center of the stretcher 20'. In case of the air filter unit 100', a membrane 21' for expanding a filter 10 formed of an elastic material is positioned at the center. Specifically, the elastic material or the membrane 21' is at least partially connected to the first wall 27'. If the entire outer circumference of the elastic material or the membrane 21' is connected to the first wall 27' or if the outer circumference of the elastic material or the membrane 21' is connected to the first wall 27' at equal intervals, there is advantage, as described above, in that the elastic material or the membrane 21' may be isotropically expanded.

At least one connection hole 32 is connected to the partition wall 25'. The connection hole 32' provides a path through which air (or fluid) can pass between the first space A and the second space B. At this point, at least a portion of the second space B is formed by the first wall 27'.

A sealing member 31' is installed in the first space A. The sealing member 31' functions to seal, from the outside, the hollow hole, that is, the first space A and the second space B. Thus, the air in the first space A and the second space B may move between the first space A and the second space B through a connection hole 32', but may not escape to the outside or may not enter into the first space A and the second space B. The sealing member 31' is connected to a lever 35' and the sealing member 31' moves according to an operation on the level 35'.

Meanwhile, the lever 35' is installed outside the variable part 26'. As shown in FIG. 8, the lever 35' is installed so as to be operable by a user from the outside through a lever hole 30' of the variable part 26'. However, the embodiment of the present invention is not limited thereto, and when the movement of the sealing member 31' can be controlled, the lever may have other shapes.

Although not shown, a hook or the like which may adjust a step may be installed to the lever 35'. The hook functions to semi-fix the lever 35' and cause a user to recognize a step change.

When the sealing member 31' moves (d) from a first position $P_1$ to a second position $P_2$, the space sealed by sealing member 31' in the first space A, and thus, the air in the second space B escapes to the first space A through the connection hole 32'. Thus, the first wall 27' formed of elastic material extends to the inside of the second space B. Since an elastic material or the membrane 21' is connected to the first wall 27', the elastic material or the membrane 21' is expanded according to extension of the first wall 27'. Conversely, when the sealing member 31' moves from the second position P2 to the first position P1, it is obvious that a reverse process is performed. That is, when the sealing member moves from the second position P2 to the first position P1, the air in the second space B flows into the first space A and the first wall 27' is contracted in the reverse direction from the second space B. As the first wall 27' is contracted in the reverse direction from the second space B, the elastic material is recovered to the original state while the force by which the elastic material is expanded by the first wall 27' is lowered.

Meanwhile, a stop member 34' is formed inside the second wall 28'.

Although not described herein, it is also possible, like the air filter unit of an embodiment, to borrow the fixed wall or the fixed frame for an air filter unit of another embodiment.

Figure 11:
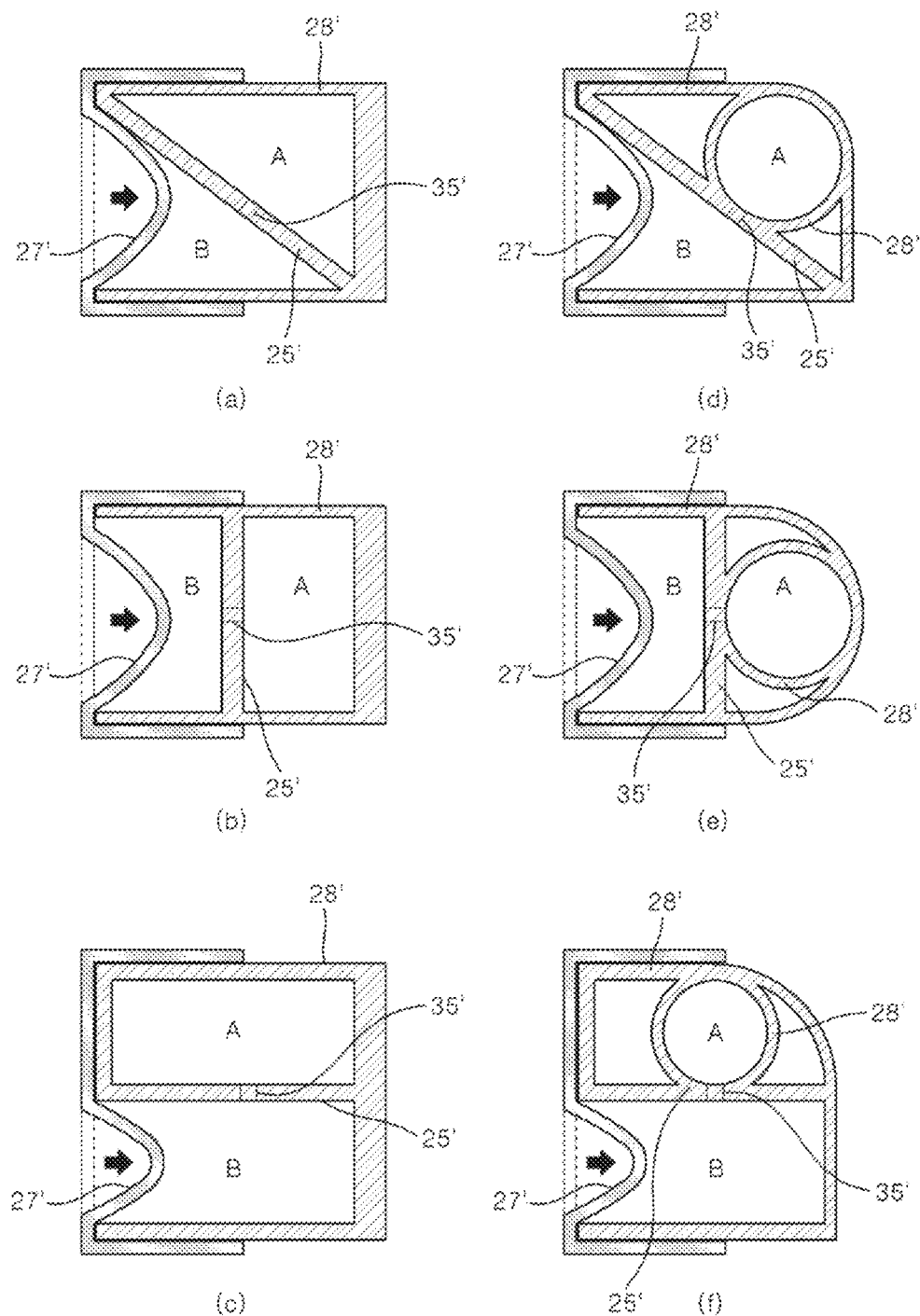
FIG. 11 is a schematic cross-sectional view of a stretcher for an air filter unit according to another embodiment of the present invention and illustrates various implemented forms.

FIG. 11 is a schematic cross-sectional view of a stretcher for an air filter unit according to another embodiment of the present invention and illustrates various implemented forms. As shown in FIG. 11(*a*), the partition wall 35' may be formed diagonally across the hollow hole, or as shown in FIG. 11(*b*), the partition wall 35' may be formed horizontally across the hollow hole, or be formed, as shown in FIG. 11(*c*), vertically across the hollow hole.

Meanwhile, as shown in. FIGS. 11(*a*) to 11(*c*), when there is an acute angle portion on an outer wall constituting the first space A, it is difficult to seal the first space A by the sealing member 31'. That is, it is highly likely that air leakage occurs in the acute angle portion of the outer wall constituting the first space A. Accordingly, as shown in FIGS. 11(*d*) to 11(*d*), the cross-section of the outer wall constituting the first space A may be configured by only dull angles without an acute angle, or be configured to be a circle or an ellipse. That is, the cross-section of the first space A may be any one among a polygon composed of dull angles, a circle, or an ellipse. At this point, a portion of the second wall 28' may serve as an outer wall of the first space A, and other portions may function as a housing. Also in this case, the first space a and the second space B are configured so that air may move between the spaces through the connection hole 32'. Meanwhile, the first space A may be formed as a separate tube.

In order to implement the air filter units 100 and 200 according to the present invention, the filter 10 the filtering capability and permeability of which may be adjusted by the stretchers 20 and 20' is necessary.

An elastic fiber filter or an elastic layer filter having pores formed therein may be used as the filter 10 the filtering capability and permeability of which may be adjusted by the stretchers 20 and 20', but the embodiment of the present invention is not limited thereto.

Figure 12:
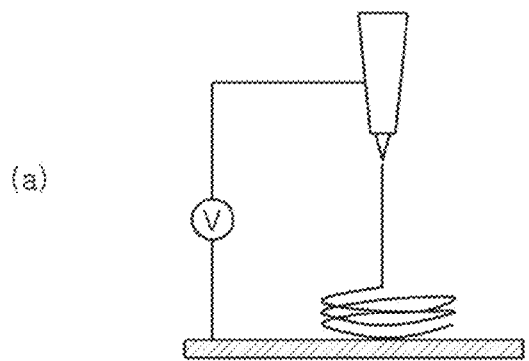
FIG. 12(a) is a schematic diagram of electro spinning for manufacturing an elastic fiber filter which is one example of an elastic fiber filter used for an air filter unit according to the present invention.
FIG. 12(b) is a photograph of the elastic fiber filter manufactured through an electro spinning method of FIG. 12(a)
FIG. 12(c) is a scanning electron microscope (SEM) image of the elastic fiber filter.
Figure 12:
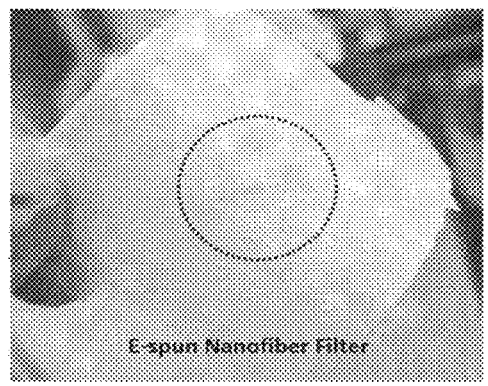
Figure 12:
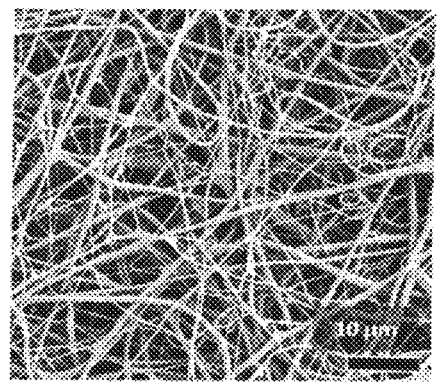

First, referring to FIG. 12, an elastic fiber filter will be described. FIG. 12(*a*) is a schematic diagram of electro spinning for manufacturing an elastic fiber filter which is one example of an elastic fiber filter used for an air filter unit according to the present invention, FIG. 12(*b*) is a photograph of the elastic fiber filter manufactured through an electro spinning method of FIG. 12(*a*), and FIG. 12(*c*) is a scanning electron microscope (SEM) image of the elastic fiber filter.

Conventional fiber filters are mostly manufactured by a melt-blowing (M/B) method. An M/B filter is manufacture by melting a thermoplastic polymer such as polypropylene, polystyrene, polyester, polyurethane, polyamids, polyethylene, or polycarbonate, and extruding and spinning the melted polymer through a nozzle. That is, the M/B method means a filter production technology in which high-pressure air is applied to polymers that are being melted and spun, the melted and spun polymers are stacked on a conveyor belt in an ultrafine state, are coupled by self adhesiveness due to residual heat, and are then manufactured in a nonwoven fabric form. However, such the M/B method can be applied only to an inelastic material, and the M/B method is difficult to be applied to the manufacturing of an elastic fiber filter that is to be used in the present invention.

Accordingly, in the present invention, an elastic fiber filter is manufactured by using an electro-spinning (E-spinning) method. As shown in FIG. 12(*a*), an E-spinning method is performed by discharging a polymer solution through a nozzle in a state of applying an electric field. At this point, when a high voltage is applied to a nozzle tip, liquid phase polymer droplets are each extended in a conical shape due to mutual electrostatic repulsive force between surface charges and coulomb force applied by an external electric field, and then the polymer solution is spun in a very thin shape. While the spun polymer solution is extended before reaching a screen and a solvent is simultaneously volatized, fibers (see FIG. 12(b) and FIG. 12(c)) arbitrarily aligned on the screen may be obtained. Such the E-spinning method has advantage in that there are less limitations in selecting materials. Accordingly, an elastic fiber filter may be manufactured through the E-spinning method using poly(styrene-co-butadiene) (SBS) or poly(dimethyl siloxane) (PDMS). In addition, since there is no limit in material selection, dust collection capability can be improved not by using only one-type polymer, but by adding a material such as poly (vinylidene fluoride) (PVDF) having high electric dipole moment. That is, an elastic fiber filter may be manufactured using different-type polymer materials.

As shown in FIG. 12(c), in an elastic fiber filter according to the present invention, fibers are configured by a single layer or multiple layers in parallel directions or in indeterminate directions. That is, pores 12 are formed by fibers, and particles are removed by a filter while air passes through pores. Since each of the fibers is an elastic body in a fiber filter according to the present invention, when the elastic fiber filter is expanded by a membrane, pores are expanded and air may more easily pass.

First of all, an elastic filter according to the present invention is characterized by being a nano particle free as shown in FIG. 12(c). Korean Patent Publication No. 10-2020-0031376 relates to a membrane in which is coupled a hierarchical structure formed by mutually perpendicular growth of two-dimensional shape metal organic structures, and Korean Patent. No. 10-2039243 relates to a multifunctional mask including silver-silica composite and carbonic fibers, but the two prior art documents both have problems in that solid nanoparticles are highly likely to deviate from fibers. Inhaling such solid nanoparticles may be the same as direct inhalation of PM or more dangerous than that. Unlike this, an elastic fiber filter according to the present invention is formed as a uniform elastic body in a manufacturing process, and nanoparticles are not formed in a manufacturing process like the conventional M/B method. Thus, in an elastic fiber filter according to the present invention, risk due to nanoparticles is prevented by achieving nanoparticle free.

Figure 13:
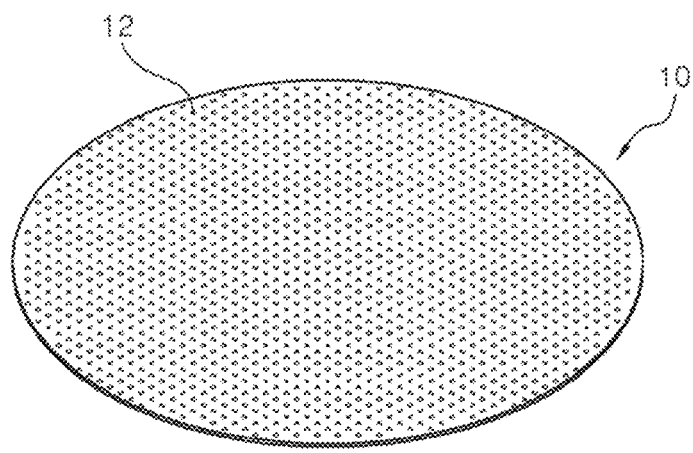
FIG. 13 is a perspective view of an elastic layer filter having which is another example of an elastic filter used for an air filter unit according to the present invention, and which has pores formed therein.
Figure 14:
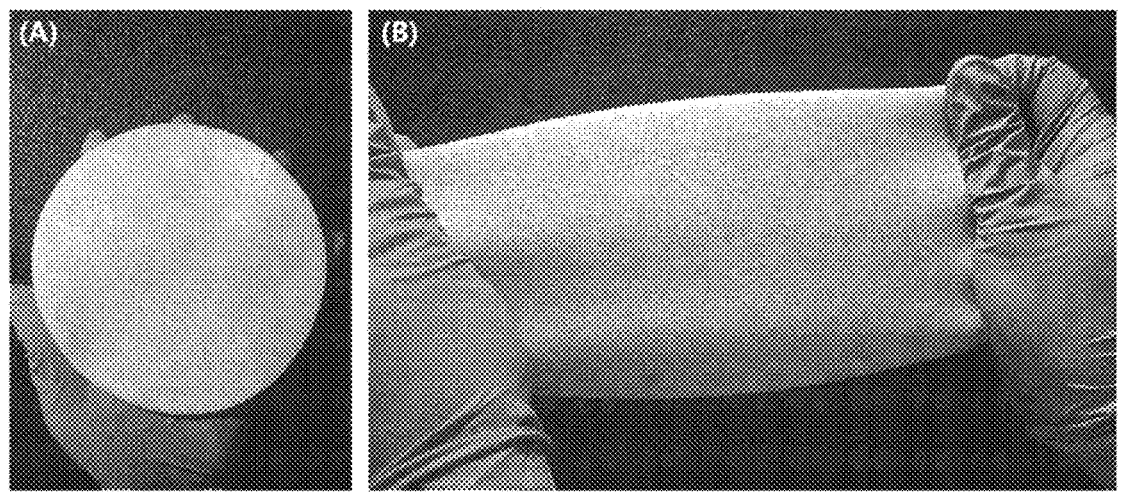
FIG. 14 is an optical microscopic photograph of an elastic layer filter.
Figure 15:
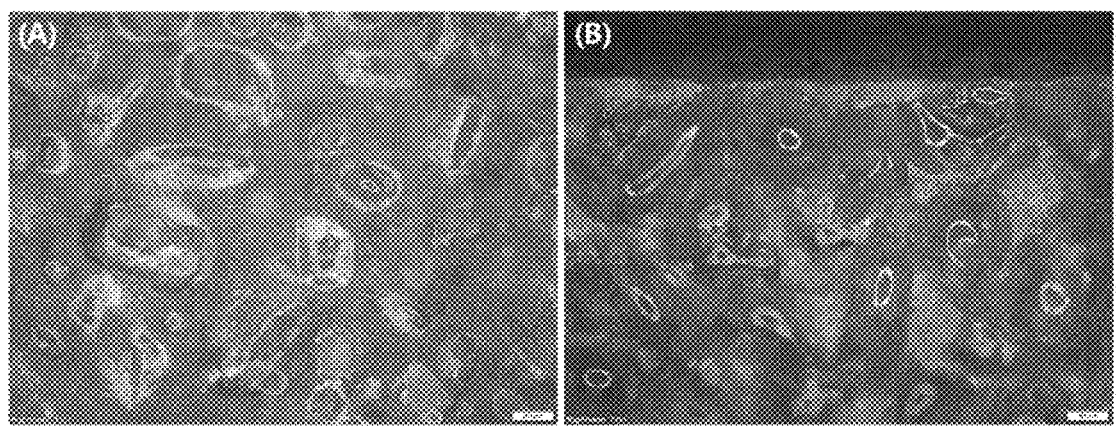
FIG. 15 is an optical microscopic photograph of an elastic layer filter.

Next, referring to FIGS. 13 to 15, an elastic layer filter may be used as a filter 10. An elastic layer filter, in which poly(styrene-co-butadiene) (SBS), poly(dimethyl siloxane) (PDMS), ECOFLEX™, or the like are formed in a single layer or multilayer and pores 12 are finely formed, may be used as an elastic layer. When the elastic layer filter is expanded by a membrane, pores are expanded and air may more easily pass. FIG. 14 is a photograph of an elastic layer filter, and when comparing FIG. 14(a) and FIG. 14(b), it may be confirmed that the elastic layer filter is elastically stretched. FIG. 15 is a plan photograph (a) and a cross-sectional photograph which are captured by an optical microscope, and it may be confirmed that micrometer-level pores are formed an the elastic layer filter.

In addition, in the present invention, it may also be possible to use the above-described fiber filter and the elastic layer filter in a composite manner. Meanwhile, in another example of the present invention, it is also possible to add antimicrobial material to a filter itself in order to impart disinfection function. The antimicrobial materials may include a metal ion such as Ag, Cu, or Zn having antimicrobial property, or any one antimicrobial polymer selected from the group consisting of hydroxyl, carboxyl, amino, phosphonium salts, ammonium salts, phenol groups, chitosan derivatives, polyamides, polyesters, and polyurethanes.

Figure 16:
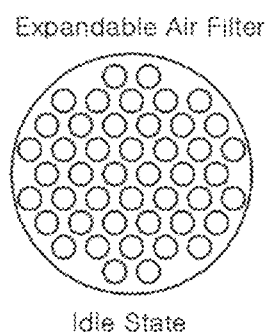
FIG. 16 is a referential view for explaining a change according to pore sizes before ((a)) and after ((b)) expansion of an elastic filter used for an air filter unit according to an embodiment of the present invention.
Figure 16:
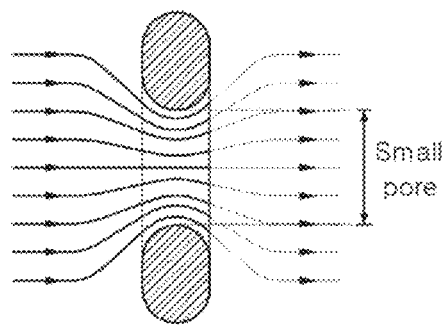
Figure 16:
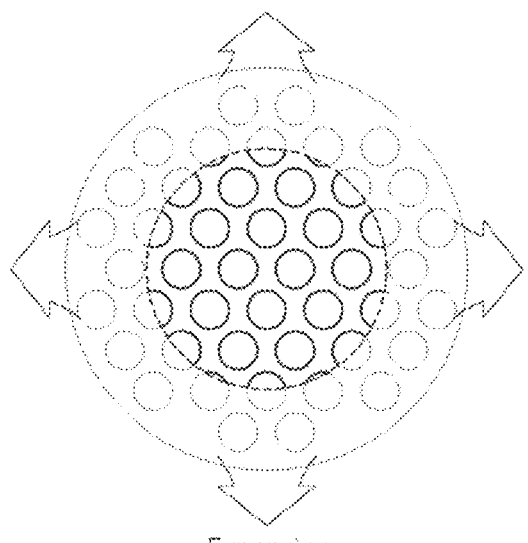
Figure 16:
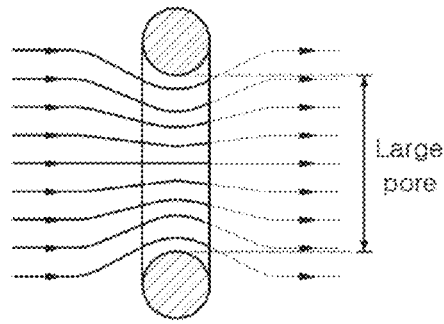
Figure 18:
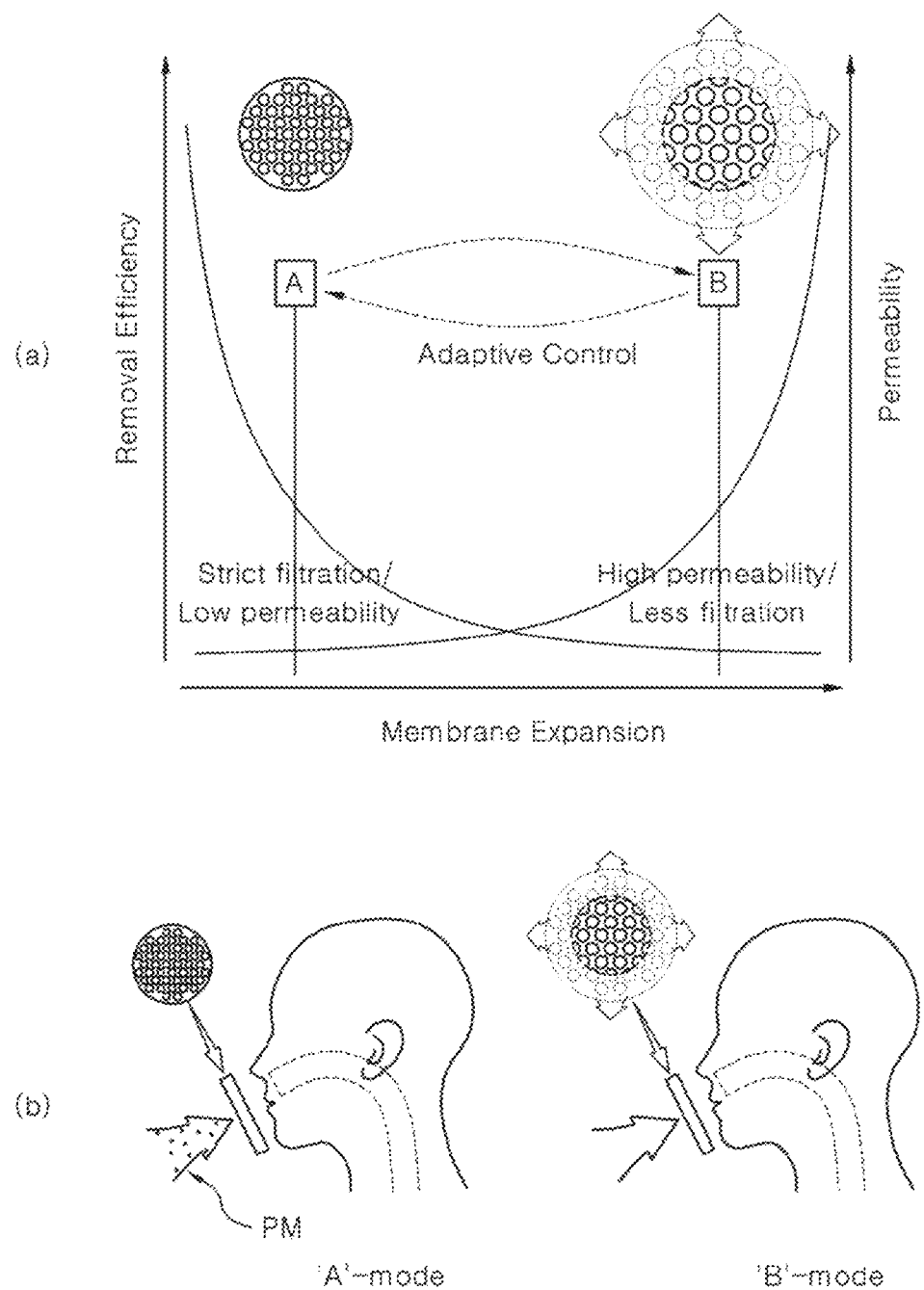
FIG. 18(a) is a graph for explaining relationship between the efficiency and permeability of a filter according to membrane expansion.
FIG. 18(b) is a referential view for explaining A-mode (filter efficiency prioritized mode) and B-mode (permeability prioritized mode).

FIG. 16 is a referential view for explaining a change according to pore sizes ((a)) and after ((b)) expansion of an elastic filter used for an air filter unit according to an embodiment of the present invention, and FIG. illustrates a simulation for flow quantity at the same pressure difference before ((a)) and after ((b)) expansion of an elastic filter used for an air filter unit according to an embodiment of the present invention. In addition, FIG. 18(a) is a graph for describing relationship between the efficiency and permeability of a filter according to membrane expansion, and FIG. 18(b) is a referential view for describing A-mode (filter efficiency prioritized mode) and B-mode (permeability prioritized mode).

Figure 17:
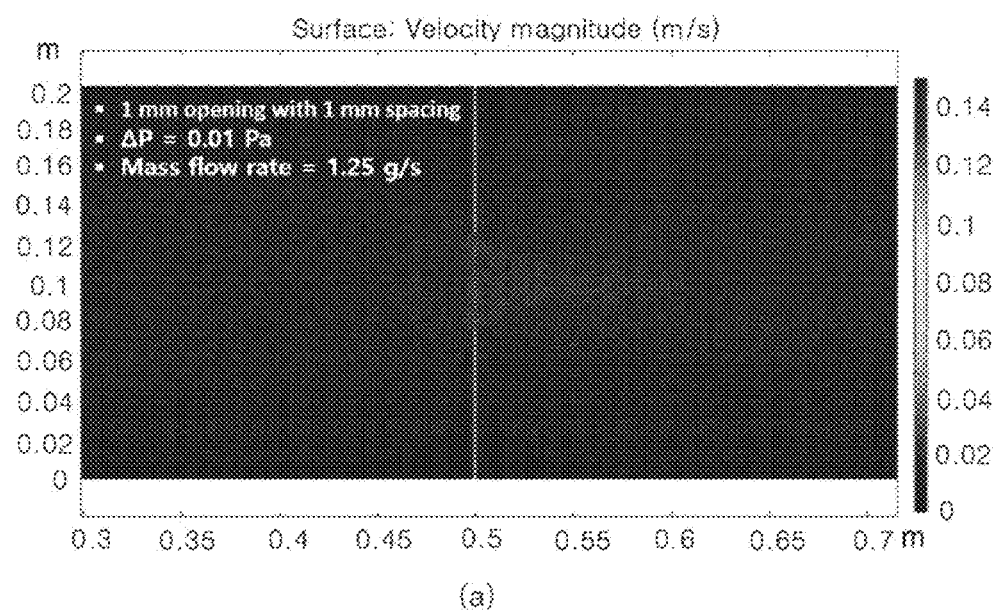
FIG. 17 illustrates a simulation for flow quantity at the same pressure difference before ((a)) and after ((b)) expansion of an elastic filter used for an air filter unit according to an embodiment of the present invention.
Figure 17:
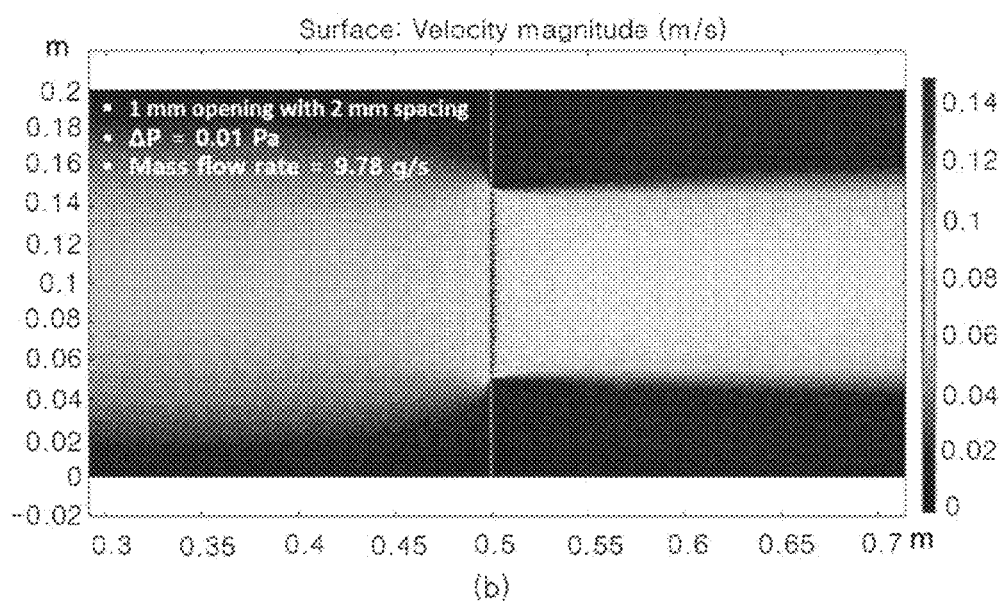

Effects of an air filter unit 100 according to an embodiment of the present invention are as the following. An air filter unit 100 according to the present invention may improve filtering performance by reducing the pore sizes of a filter and lowering flow velocity as shown in A-mode of FIGS. 17(a) and 18(b). By comparison, an air filter unit 100 according to the present invention can also increase permeability by increasing the pore sizes of a filter as shown in B-mode of FIGS. 17(a) and 18(b). That is, operation characteristic of the air filter unit 100 according to an embodiment of the present invention may be optimized according to peripheral environments or needs of a wearer. As can be found in FIG. 17, it may be confirmed that when the pore size of a filter is doubled, flow quantity increases eight times even under the same pressure difference. That is, it may be found that permeability can be adjusted. Consequently, as shown in the graph of FIG. 18(a), it is possible to actively respond to peripheral environments and user's demands by adjusting a stretcher 20 to adjust the expansion or contraction of a membrane 21. For example, when using a PM (Particulate Matter) sensor and a logic circuit, filtering performance may be improved by reducing the pore size in a place of strong air pollution, and aspiratory burden may be minimized by increasing permeability when moving to a place of small air pollution.

Figure 19:
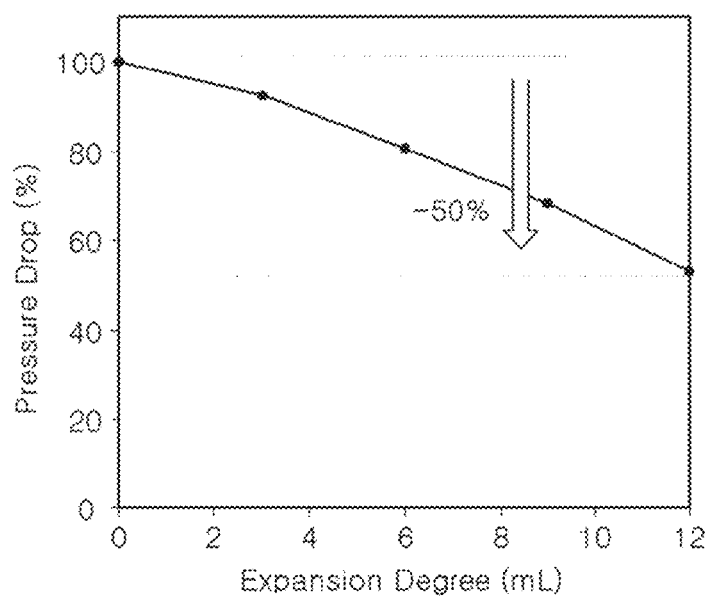
FIG. 19 is a graph in which a pressure difference for achieving the same flowrate before and after a filter is measured while expanding an elastic filter used for an air filter unit according to an embodiment of the present invention.

FIG. 19 is a graph in which a pressure difference for achieving the same flowrate before and after a filter is measured while expanding an elastic fiber filter used for an air filter unit according to an embodiment of the present invention.

Referring to FIG. 19, it may be found that when increasing the pore size by expanding a filter, a pressure difference for passing the same flowrate of air is reduced by approximately 50% or more compared to a case in which the pore size is minimized. This means that when applying, to a mask, an air filter unit 100 according to an embodiment of the present invention, a wear may conveniently breathe as much.

Figure 20:
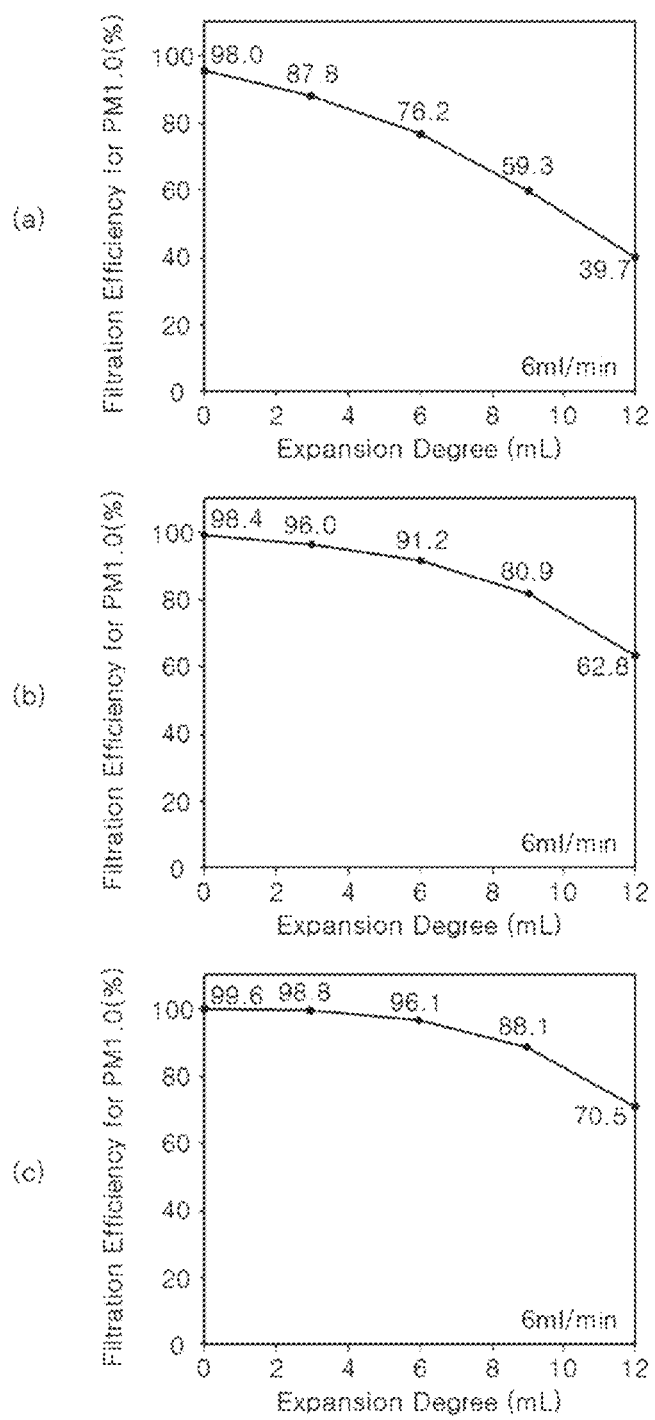
FIG. 20 illustrates measurements of filter efficiency while expanding an elastic filter used for an air filter unit according to an embodiment of the present invention, and the measurements were obtained on the basis of (a) $PM_{1.0}$, (b) $PM_{2.5}$, and (c) $PM_{3.0}$.

FIG. 20 illustrates measurements of filter efficiency while expanding an elastic filter fiber used for an air filter unit according to an embodiment of the present invention, and the measurements were obtained on the basis of (a) $PM_{1.0}$, (b) $PM_{2.5}$, and (c) $PM_{3.0}$. This experiment was performed under a very harsh environment.

Referring to FIG. 20, it may be found that in case of PM3.0 particles, approximately 99.6% of particles can be removed in a state in which the pore size is maximally reduced, and even when the pore size is maximally increased, approximately 70.5% of particles can be removed. From this, it may be found that fine dusts are still removed by a high level compared to the case of FIG. 19, in which a required pressure drops to the level of approximately 50%. It may be found that also in case of PM2.5 particles, approximately 98.4% of particles can be removed in a state in which the pore size is maximally reduced, and even when the pore size is maximally increased, approximately 70.5% of particles can be removed. It may be found that in case of PM1.0 particles, approximately 95.0% of particles can be removed in a state in which the pore size is maximally reduced, and even when the pore size is maximally increased, approximately 39.7% of particles can be removed. This data is provided to qualitatively verify the basis configuration of the present invention, which is a change in permeability and efficiency according to expansion of an air filter unit 100, and the numerical values are not absolute. The filter 10 of the air filter unit 100 used for data acquisition is in a stage before optimization, it is expected to reach the level according to Korean certifications (KF 99, KF 94, etc.) without difficulty through later research.

Figure 21:
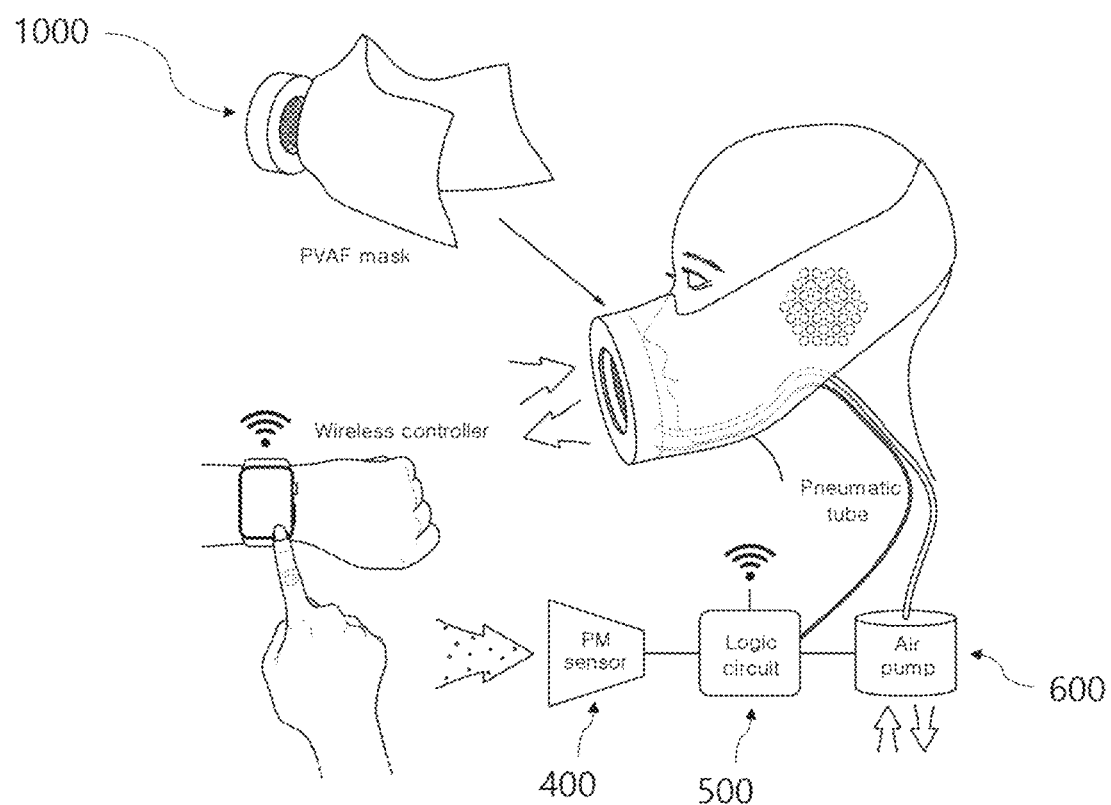
FIG. 21 is a referential view illustrating a schematic perspective view of a mask according to another embodiment of the present invention and a state in which the mask is worn.

FIG. 21 is a referential view illustrating a schematic perspective view of a mask according to another embodiment of the present invention and illustrating a state in which the mask is worn.

Referring to FIG. 21, a mask 1000 according to another embodiment of the preset invention includes: an air filter unit 100, a mask body 200 which covers the nose and mouth of a wearer and to which the air filter unit 100 is installed; and a fixing member 300 that is formed on both sides of the body 200 and fixes the body 200 to the face of the wearer. An air filter unit 100 according to the above-described embodiment of the present invention is used as the air filter unit 100, and the descriptions on overlapped. portions will be omitted. The fixing member 300 may hare not only a shape of being hooked to the ears, but also a shape surrounding the head of a user, and the embodiment of the present invention is not limited thereto. That is, a fixing member 300 is sufficient as long as the fixing member 300 may cause the mask body 200 to cover the nose and mouth of a wearer.

The wearer may adjust the filtering capability and permeability of the mask 1000 by adjusting the air filter unit 100. For example, when using the above-described stretcher 20, pores of the filter 10 may be expanded or contracted by expanding or contracting a membrane 21 by discharging or injecting air into a hollow hole S through a tube.

In addition, the filtering capability and permeability of the mask can actively be adjusted in linkage with a device (for example, a PM sensor or a smartphone) that may sense or inform an external environment. As shown in FIG. 21, a mask 1000 according to another embodiment of the present invention may further be provided with a PM sensor 400, a logic circuit 500, and a pump 600, and when the PM sensor 400 detects a state of peripheral air, air may be injected into or discharged from a hollow hole by operating the pump 600.

Figure 22:
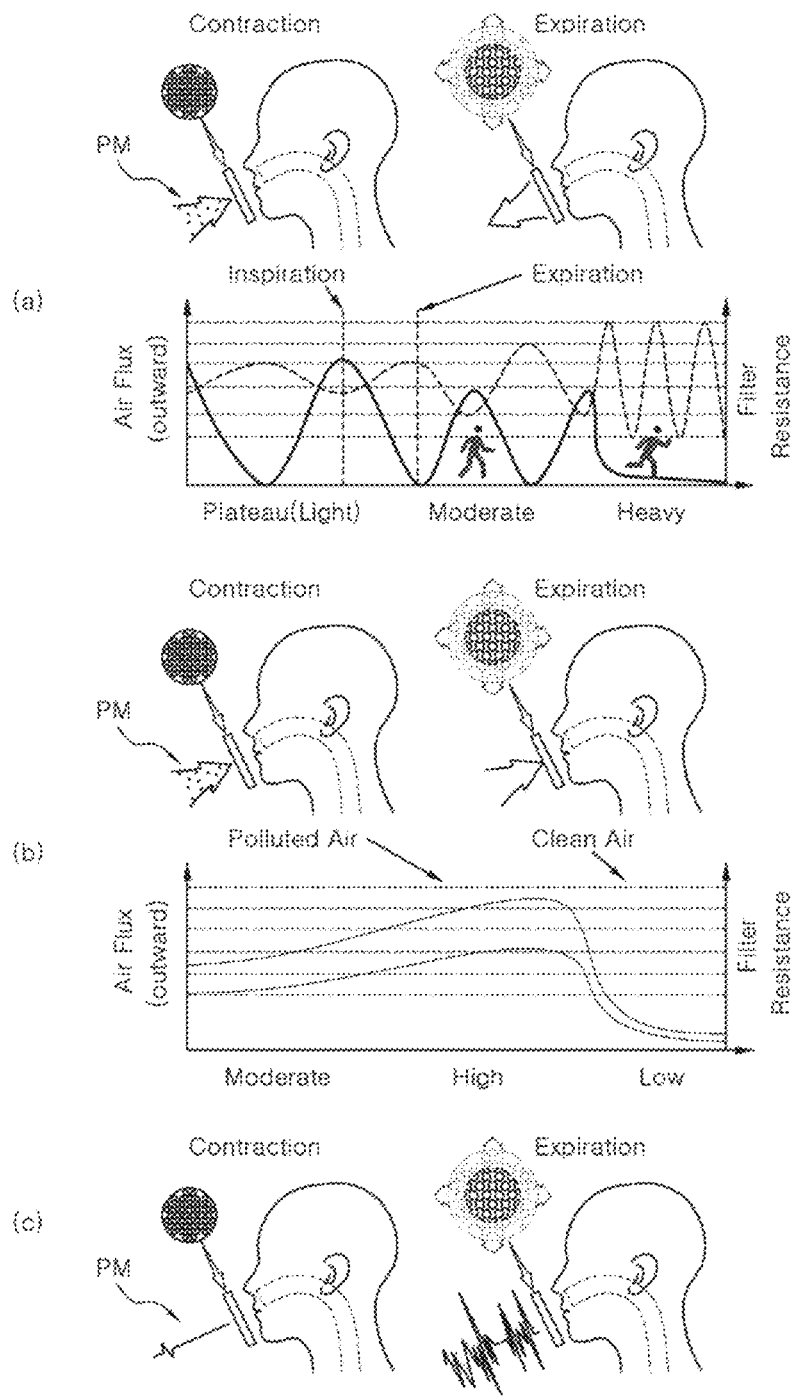
FIG. 22 is a referential view for explaining that permeability of a mask is adjusted according to a peripheral state or a state of a wearer.

FIG. 22 is a referential view for explaining that permeability of a mask is adjusted according to a peripheral state or a state of a wearer.

FIG. 22(a) illustrates an operation of a mask 1000 during normal time and an exercise state, and the filtering capability may be improved during normal time by narrowing pores and permeability may be improved by expanding the pores when a user takes exercise. First of all, since a mask 1000 according to the present invention is capable of continuously adjusting the pore size, the filtering capability and the pore size can be adjusted by adjustment to a suitable pore size in an intermediate-level exercise state. FIG. 22(b) illustrates an operation of a mask 1000 according to peripheral air state, and the filtering capability may be improved by reducing the pore size when the air state is bad, and permeability may be ensured by expanding the pores when the air state is good. In particular, when the mask 1000 is in linkage with a PM sensor or a smartphone, the mask 1000 may adjust the filtering capability and permeability of the mask 1000 actively in linkage with air quality. FIG. 22(b) illustrates an operation of a mask 1000 during normal time and conversation, convenience of aspiration may be enhanced and communication power of conversation may be improved by expanding pores during conversation. Meanwhile, the operation of the mask 1000 explained in FIG. 22 may be performed by using a logic circuit 500 and a pump 600.

Figure 23:
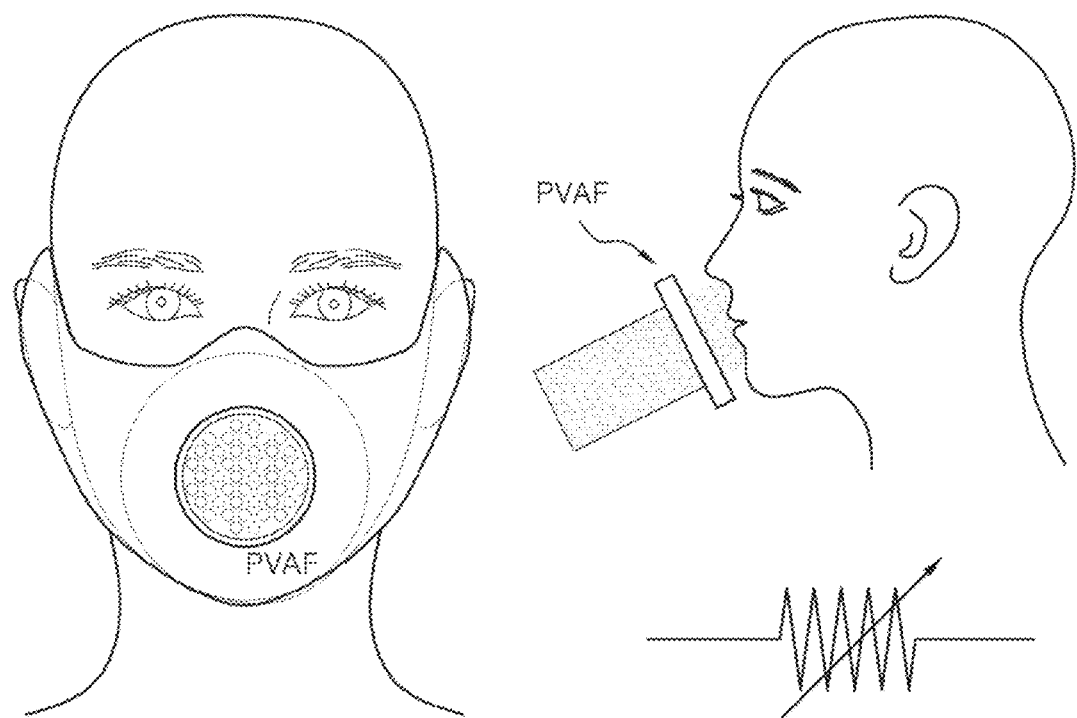
FIG. 23 illustrates a first implemented form of a mask according to another embodiment of the present invention.
Figure 24:
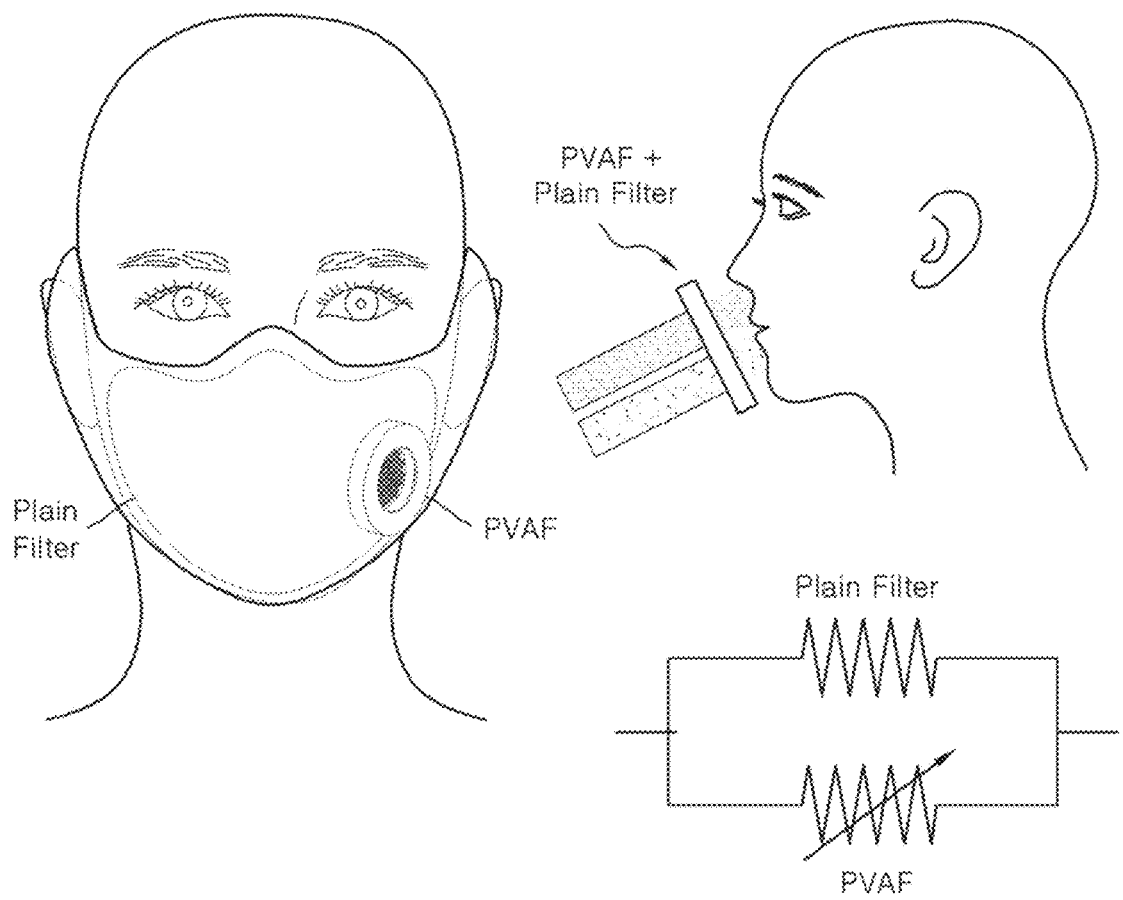
FIG. 24 illustrates a second implemented form of a mask according to another embodiment of the present invention.

FIG. 23 illustrates a first implemented form of a mask according to another embodiment of the present invention, and FIG. 24 illustrates a second implemented form of a mask according to another embodiment of the present invention. The acronym, "PVAF", used in FIGS. 23 and 24 represents Permeability Variable Air Filter.

The mask 1000 of the first implemented form is of a type in which a mask body 200 does not have permeability and only an air filter unit 100 has permeability. That is, in the first implemented form, filtering capability and permeability are adjusted by the air filter unit 100.

Conversely, in the mask of the second implemented form, the mask body 200 is formed of a material that has permeability and simultaneously has filtering capability. In this case, filtering is performed while air is introduced into the mask body 200 and the air filter unit 100, but the filtering capability and the permeability may be adjusted by the air filter unit 100.

In this case, a permeable control layer is provided instead of the filter, and permeability is adjusted by expanding or contracting the permeable control layer by means of a stretcher in at least one direction. That is, pores through which air passes are formed in the permeable control layer, and the permeable control layer is formed of an elastic material, and thus, the pore size is changed by an operation of the stretcher and permeability is adjusted. For example, a permeable control layer in which pores are formed in an elastic layer by laser drilling may be used. In addition, the pores of the permeable control layer may be larger than the pores of a filter.

The scope of the present invention is not limited by the examples and descriptions specifically described so far. Furthermore, it is stated once more that the scope of the present invention should not be construed to be limited by an obvious change or a substitution in the field to which the present invention pertains.

The invention claimed is:

1. A stretcher capable of expanding an elastic material located at a center thereof, the stretcher comprising: a variable part installed around the elastic material and configured to pull at least one side of the elastic material and expand the elastic material, wherein the variable part comprises:
  a first wall connected to the elastic material and having elasticity;
  a second wall constituting a hollow hole together with the first wall;
  a partition wall configured to partition the hollow hole into a first space and a second space;
  one or more connection holes formed in the partition wall so that air is able to move between the first space and the second space; and
  a sealing member installed in the first space and configured to seal the first space and the second space from an outside,
  wherein the first wall is extended toward the hollow hole as air escapes from the hollow hole, and the first wall expands the elastic material as the first wall is extended toward the hollow hole, and wherein at least a portion of the second space is formed by the first wall, the first wall is extended toward the second space by injection of air from the second space to the first space according to a movement of the sealing member in one direction, and the first wall expands the elastic material as the first wall is extended toward the second space.

2. The stretcher of claim 1, wherein the first wall is contracted in a reverse direction from the second space as air in the second space is introduced into the first space according to the movement of the sealing member in the reverse direction of the one direction, and as the first wall is contracted in the reverse direction from the second space, the elastic material is recovered to an original state while a force expanding the elastic material is lowered.

3. The stretcher of claim 1, wherein a lever connected to the sealing member is installed outside the variable part, and the movement of the sealing member is controlled by an operation of the lever.

4. The stretcher of claim 1, wherein the partition wall vertically or horizontally partitions the hollow hole.

5. The stretcher of claim 1, wherein as an entire outer circumference of the elastic material is connected to the first wall or an outer circumference of the elastic material is connected to the first wall at equal intervals, and as the first wall is extended toward the hollow hole, the elastic material is isotropically expanded.

6. The stretcher of claim 1, wherein the second wall is formed so that a movement thereof is restricted according to air injected into the hollow hole.

7. The stretcher of claim 1, wherein a fixing wall or a fixing frame for restricting a movement of the second wall due to air injected into the hollow hole is installed inside or outside the second wall.

8. An air filter unit capable of adjusting permeability comprising: a filter configured to filter particles contained in passing air by pores and a stretcher capable of expanding or contracting the filter in at least one direction, wherein:
the filter is formed of an elastic material and has pores, sizes of which vary according to an operation of the stretcher;
the stretcher comprises:
a membrane in which the filter is installed; and
a variable part installed around the membrane and configured to pull at least one side of the membrane and expand the elastic material,
wherein the variable part comprises:
a first wall connected to the membrane and having elasticity;
a second wall constituting a hollow hole together with the first wall;
a partition wall configured to partition the hollow hole into a first space and a second space;
one or more connection holes formed in the partition wall so that air is able to move between the first space and the second space; and
a sealing member installed in the first space and configured to seal the first space and the second space from an outside,
wherein the first wall is extended toward the hollow hole as air escapes from the hollow hole, the first wall expands the membrane as the first wall is extended toward the hollow hole, and the pores of the filter are expanded depending on an expansion of the membrane, and
wherein at least a portion of the second space is formed by the first wall, the first wall is extended toward the second space by injection of air from the second space to the first space according to a movement of the sealing member in one direction, and the first wall expands the membrane as the first wall is extended toward the second space.

9. The air filter unit of claim 8, wherein the membrane comprises one or more holes which are formed in a central portion thereof and through which air passes.

10. The air filter unit of claim 8, wherein a central portion of the membrane is formed in a mesh shape, and the filter makes close contact with the mesh-shape portion.

11. The air filter unit of claim 8, further comprising:
a lid installed on a front surface of the filter and spaced apart from the filter; and
a lamp installed inside the lid and configured to irradiate the filter with ultraviolet.

12. The air filter unit of claim 8, wherein the first wall is contracted in a reverse direction from the second space as air in the second space is introduced into the first space according to the movement of the sealing member in the reverse direction of the one direction, and as the first wall is contracted in the reverse direction from the second space, the membrane is recovered to an original state while a force expanding the membrane is lowered.

13. The air filter unit of claim 8, wherein a lever connected to the sealing member is installed outside the variable part, and the movement of the sealing member is controlled by an operation of the lever.

14. The air filter unit of claim 8, wherein the partition wall vertically or horizontally partitions the hollow hole.

15. The air filter unit of claim 8, wherein as an entire outer circumference of the membrane is connected to the first wall or an outer circumference of the membrane is connected to the first wall at equal intervals, and as the first wall is extended toward the hollow hole, the membrane is isotropically expanded.

16. A mask comprising:
a mask body configured to cover the nose and mouth of a wearer;
an air filter unit installed to the mask body; and
a fixing member formed on both sides of the body and configured to fix the body to a face of the wearer,
wherein:
the air filter unit comprises a filter configured to filter particles contained in passing air by pores and a stretcher capable of expanding or contracting the filter in at least one direction, the filter,
the filter is formed of an elastic material and has pores, sizes of which vary according to an operation of the stretcher,
the stretcher comprises: a membrane in which the filter is installed; and a variable part installed around the membrane and configured to pull at least one side of the membrane and expand the elastic material,
the variable part comprises:
a first wall connected to the membrane and having elasticity;
a second wall constituting a hollow hole together with the first wall;
a partition wall configured to partition the hollow hole into a first space and a second space;
one or more connection holes formed in the partition wall so that air is able to move between the first space and the second space; and
a sealing member installed in the first space and configured to seal the first space and the second space from an outside, the first wall is extended toward the hollow hole as air escapes from the hollow hole, the first wall expands the membrane as the first wall is extended toward the hollow hole, and the pores of the filter are expanded depending on an expansion of the membrane, and at least a portion of the second space is formed by the first wall, the first wall is extended toward the second space by injection of air from the second space to the first space according to a movement of the sealing member in one direction, and the first wall expands the elastic material as the first wall is extended toward the second space.

17. The mask of claim 16, wherein the mask body has a permeability and is formed of a material capable of filtering particles.

18. The mask of claim 16, further comprising:
a sensor configured to detect a state of peripheral air; and
a pump configured to inject air into or absorb air from the hollow hole, whereinthe pump injects air into the hollow hole or absorbs air from the hollow hole according to the state of peripheral air, and increases or lowers permeability of the air filter unit.

* * * * *